US011879881B2

(12) United States Patent
Lebegue

(10) Patent No.: US 11,879,881 B2
(45) Date of Patent: Jan. 23, 2024

(54) METHOD FOR CALIBRATING A GAS SENSOR

(71) Applicant: ELICHENS, Grenoble (FR)

(72) Inventor: Benjamin Lebegue, Grenoble (FR)

(73) Assignee: ELICHENS, Grenoble (FR)

( * ) Notice: Subject to any disclaimer, the term of this patent is extended or adjusted under 35 U.S.C. 154(b) by 242 days.

(21) Appl. No.: 17/416,057

(22) PCT Filed: Dec. 17, 2019

(86) PCT No.: PCT/FR2019/053130
§ 371 (c)(1),
(2) Date: Jun. 18, 2021

(87) PCT Pub. No.: WO2020/128311
PCT Pub. Date: Jun. 25, 2020

(65) Prior Publication Data
US 2022/0099640 A1    Mar. 31, 2022

(30) Foreign Application Priority Data
Dec. 19, 2018 (FR) ........................................ 1873407

(51) Int. Cl.
*G01N 33/00* (2006.01)
(52) U.S. Cl.
CPC ..... *G01N 33/0006* (2013.01); *G01N 33/0075* (2013.01)
(58) Field of Classification Search
CPC ........... G01N 33/0006; G01N 27/4175; G01N 33/0075; G01N 33/0073
(Continued)

(56) References Cited

U.S. PATENT DOCUMENTS 6,252,510 B1 * 6/2001 Dungan ............. G01N 33/0075
340/539.1
6,490,530 B1 * 12/2002 Wyatt ..................... G08B 21/14
702/26

(Continued)

FOREIGN PATENT DOCUMENTS

CN      105510535 A  *  4/2016
FR        2984575 A1 *  6/2013  ............. G01D 4/006

(Continued)

OTHER PUBLICATIONS

Hasenfratz et al. "On-the-Fly Calibration of Low-Cost Gas Sensors" Intelligent Virtual Agent. IV A 2015. LNCS; [Lecture Notes in Computer Science; Lect. Notes Computer]. Springer. Berlin, Heidelberg. pp. 228-244 (Feb. 2012).

(Continued)

*Primary Examiner* — David A. Rogers
(74) *Attorney, Agent, or Firm* — TraskBritt

(57) ABSTRACT

A method for calibrating a gas sensor includes associating a reference station with the gas sensor, the latter belonging to a network of sensors distributed between various positions in a geographical region and being configured to measure a concentration of an analyte in the air at various measurement times. The geographical regions comprises reference station(s) remote from the gas sensor and configured to measure, at various reference times, a concentration of the analyte in the air. During a calibration time slot, an analyte concentration is measured with the gas sensor, taking into account an analyte concentration measured by the reference station associated with the gas sensor. From the analyte concentration measured by the reference station in the calibration time slot, an analyte concentration in the position of the gas sensor is estimated. The estimated analyte con- (Continued)

centration and the analyte concentration measured by the gas sensor are compared.

13 Claims, 4 Drawing Sheets

(58) Field of Classification Search
USPC .............................. 73/1.02, 1.03, 1.06, 1.07
See application file for complete search history.

(56) References Cited

U.S. PATENT DOCUMENTS

| | | | |
|---|---|---|---|
| 7,080,544 B2 * | 7/2006 | Stepanik | G08B 21/12 |
| | | | 702/22 |
| 9,291,608 B2 * | 3/2016 | Herzl | G01N 33/0006 |
| 9,588,031 B2 * | 3/2017 | Knochenmuss | G01N 15/02 |
| 9,683,977 B2 * | 6/2017 | Liu | G08B 21/14 |
| 10,429,367 B2 * | 10/2019 | Crescini | H02J 7/35 |
| 10,487,651 B2 * | 11/2019 | Dursun | E21B 49/08 |
| 10,725,008 B2 * | 7/2020 | Dong | G01N 35/00871 |
| 10,928,295 B2 * | 2/2021 | McBrady | G01N 15/0205 |
| 11,060,972 B2 * | 7/2021 | Caritu | G01N 21/3151 |
| 11,408,877 B2 * | 8/2022 | Zanini | G01N 33/0075 |
| 11,467,147 B2 * | 10/2022 | Lascaux | G01N 27/3274 |
| 11,727,519 B1 * | 8/2023 | Foiles | G01W 1/10 |
| | | | 73/170.16 |
| 11,733,221 B2 * | 8/2023 | Armitage | G01N 33/0009 |
| | | | 340/855.1 |
| 2017/0184560 A1 * | 6/2017 | Crescini | G01N 33/0031 |
| 2018/0136180 A1 | 5/2018 | Chou | |
| 2018/0156766 A1 | 6/2018 | Zeng et al. | |
| 2020/0003742 A1 * | 1/2020 | Dong | G01N 35/00871 |
| 2020/0025738 A1 * | 1/2020 | Lascaux | G01N 33/0031 |
| 2020/0378940 A1 * | 12/2020 | Pariseau | G01N 33/0075 |
| 2022/0276154 A1 * | 9/2022 | Le | G01N 21/314 |

FOREIGN PATENT DOCUMENTS

| | | | | |
|---|---|---|---|---|
| WO | 2018/178561 A1 | 10/2018 | | |
| WO | WO-2018229239 A1 * | 12/2018 | | G01N 21/274 |
| WO | WO-2019145649 A1 * | 8/2019 | | G01N 21/3504 |
| WO | WO-2022049199 A1 * | 3/2022 | | G01D 4/006 |
| WO | WO-2022265562 A1 * | 12/2022 | | G01N 21/274 |

OTHER PUBLICATIONS

International Search Report for International Application No. PCT/FR2019/053130, dated Apr. 2, 2020, 7 pages with English Translation.

International Written Opinion for International Application No. PCT/FR2019/053130, dated Apr. 2, 2020, 9 pages with English Machine Translation.

* cited by examiner

METHOD FOR CALIBRATING A GAS SENSOR

CROSS-REFERENCE TO RELATED APPLICATIONS

This application is a national phase entry under 35 U.S.C. § 371 of International Patent Application PCT/FR2019/053130, filed Dec. 17, 2019, designating the United States of America and published as International Patent Publication WO 2020/128311 A1 on Jun. 25, 2020, which claims the benefit under Article 8 of the Patent Cooperation Treaty to French Patent Application Ser. No. 1873407, filed Dec. 19, 2018.

TECHNICAL FIELD

The technical field of the disclosure is the calibration of a gas sensor intended to carry out measurements of gas in the environment, and, in particular, in an urban or peri-urban environment.

BACKGROUND

Obtaining maps describing the spatial distribution of concentrations of harmful particles or molecules is a need that must be met to meet the expectations of the populace and authorities, in particular, in sensitive geographical regions, such as urban regions or more generally in regions liable to be affected by air pollution. Many models have been developed that allow maps of air pollution to be established and how they will change over time to be predicted. These models are fed by sensors that are distributed over the examined geographical regions.

On the basis of data relating to pollutant emission sources, and in light of parameters related to topographic or meteorological conditions, the models allow the spatial distribution of concentrations of polluting particles or molecules in the environment to be established, the latter being subdivided using a spatial mesh.

Regional or national agencies operate measurement stations that are distributed over their territory, these stations being referred to as reference stations and allowing regular measurements of the concentration of atmospheric pollutants to be obtained. The latter are for example $NO_2$, $O_3$, CO, or fine particles, for example particles with a diameter smaller than or equal to 10 μm (PM10) or particles with a diameter of smaller than 2.5 μm (PM2.5). The measurements carried out by certain agencies are open, i.e., easily accessible to the public. In Europe it is, for example, possible to obtain the concentrations of these pollutants from the website of the European Environment Agency. In France, regional agencies manage measurement stations, this allowing maps of pollutants as well as forecasts to be obtained. Measurement stations are devices that are reliable, but expensive and bulky. As a result, it is difficult to envisage their deployment at the nodes of a fine spatial mesh. Their number is limited to a few units per agglomeration, and to 10 to 20 for the largest agglomerations.

However, to obtain a more precise map taking into account local particularities, locally congested traffic for example, it would be preferable to deploy a high number of measurement sensors, the latter being spaced apart by only a few hundred meters. This would allow maps that are more responsive to the occurrence of local singularities having an influence on pollutant concentrations to be obtained. Document WO2018178561, for example, describes a method for mapping an environment on the basis of sensors distributed over the nodes of a dense mesh. On account of the number of sensors used, the latter have a simpler design and a lower cost than the measurement stations described above. In contrast, it is necessary to ensure that the measured data are reliable so as to obtain maps that are as accurate as possible.

One way to verify the accuracy of the measurements delivered by sensors is to expose them to known concentrations of gas. However, this type of calibration is difficult to carry out in the field, and therefore requires the tested sensors to be moved to a laboratory, then exposed to a standard gas, before being redeployed to the field. It will be understood that this type of calibration cannot be envisioned when the number of sensors exceeds several tens of units, or several hundred units.

The disclosure addresses this problem by providing a simple method for verifying the quality of the data measured by the sensors and, if necessary, calibrating them, while keeping the sensors deployed in the field, and without handling the sensors.

BRIEF SUMMARY

A first subject of the disclosure is a method for calibrating a gas sensor, the gas sensor belonging to a network of sensors distributed between various positions in a geographical region, the gas sensor being intended to measure a concentration of an analyte in the air, the geographical region comprising at least one reference station, which is remote from the gas sensor, the reference station being intended to measure a concentration of analyte in the air, the method comprising the following steps:

a) associating at least one reference station with the gas sensor;

b) during a calibration time slot, measuring an analyte concentration with the gas sensor and taking into account an analyte concentration measured by each reference station associated with the gas sensor;

c) from the measurement of the analyte concentration measured by each reference station in the calibration time slot, estimating an analyte concentration in the position of the gas sensor;

d) comparing the analyte concentration estimated in step c) and the analyte concentration measured by the gas sensor in step b); and e) depending on the comparison made in step d), calibrating the gas sensor.

The concentration may be expressed, for example, as an amount per unit volume, or as a mass per unit volume.

According to one embodiment, the method comprises, prior to steps a) to e), a training step so as to:

select a reference station or a plurality of reference stations, from among a plurality of reference stations, such that, during the calibration time slot, the analyte concentration measured by each selected reference station is correlated with the analyte concentration in the position of the gas sensor; and determine an estimator of the analyte concentration in the position of the gas sensor from the analyte concentration measured by each selected reference station;

such that:

in step a), each reference station selected in the training step is associated with the gas sensor; and in step c), the analyte concentration in the position of the gas sensor is estimated by applying the estimator determined in the training step.

The calibration time slot may be determined in the training step. The training step may employ a neural network so as to select at least one reference station and establish the estimator and possibly the calibration time slot.

According to one preferred embodiment:

the analyte is emitted, in the geographical region, at a concentration that varies over the course of a preset time period, a day for example, the emitted analyte concentration varying between a minimum and a maximum over the course of each preset time period, over the course of each day for example;

the calibration time slot is determined so as to correspond to a minimum emission of the analyte in the geographical region in question, during each time period in question, during each day for example.

In step c), the analyte concentration in the position of the gas sensor may be:

considered to be equal to the analyte concentration measured by a reference station associated with the gas sensor; or estimated by applying a dispersion model, based on the analyte concentration measured by at least one reference station associated with the gas sensor.

The analyte may be emitted by means of transport or heating, the calibration time slot thus being comprised between midnight and 6 o'clock in the morning, and preferably between 3 o'clock in the morning and 6 o'clock in the morning.

Another subject of the disclosure is a device for estimating a concentration of an analyte in a geographical region, the device comprising:

a plurality of gas sensors distributed over the geographical region, between various positions, each gas sensor being configured to measure an analyte concentration at various measurement times, and a processing unit, which receives the measurements of at least one gas sensor; the device being characterized in that the processing unit is configured to implement a method according to the first subject of the disclosure, using at least one reference measurement station located in the geographical region.

Other advantages and features will become more clearly apparent from the following description of particular embodiments of the disclosure, which are provided by way of nonlimiting examples, and which are shown in the figures listed below.

DETAILED DESCRIPTION

Figure 1:
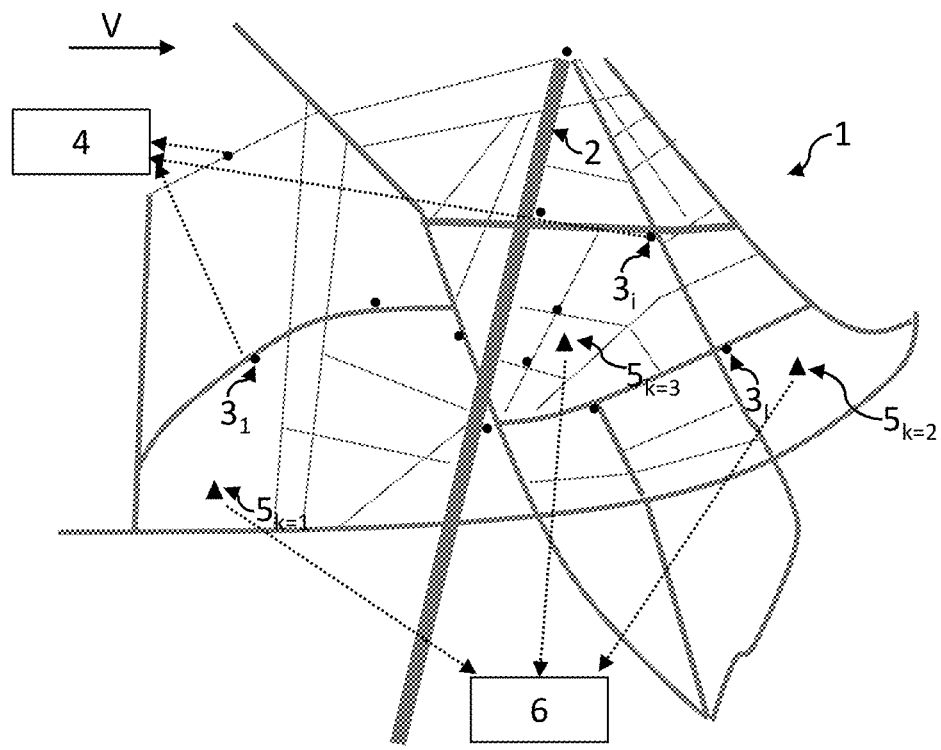
FIG. 1 schematically shows a set of elementary gas sensors forming a network of sensors covering a geographical region of interest, in which reference stations are also found.

FIG. 1 shows a geographical region in which it is desired to determine a map of a concentration of an analyte forming an atmospheric pollutant. The analyte is, for example, a gaseous species, such as CO, NO, $NO_2$, $O_3$, $SO_2$, $C_6H_6$, etc. It may also be a question of fine particles, for example PM10 or PM2.5 particles in suspension. The acronym PM, meaning particulate matter, is known to those skilled in the art. Generally, the geographical region in question contains analyte emission sources. These emission sources may be related to vehicular traffic, to the presence of district-heating plants, or to the presence of industrial plants liable to emit the analyte. The geographical region may contain an urban or peri-urban region, or an industrial zone or an airport. In the example shown in FIG. 1, the geographical region 1 is part of a city, containing streets 2 that have been drawn with dark gray lines. Gas sensors $3_1 \ldots 3_I$ are distributed over the geographical region 1. I is a natural integer designating the number of gas sensors deployed. These sensors are, for example, NDIR sensors, or electrochemical sensors, or optical sensors, or sensors with a solid substrate, made of metal oxide (MOX) for example. It may be, for example, a question of sensors such as described in WO2018162848. In FIG. 1, the gas sensors have been represented by black dots. These sensors define a mesh of the geographical region in question. The distance between two adjacent sensors is preferably smaller than 1 km, or even smaller than 500 m. It is, typically, a few hundred meters. The density of the sensors is, typically, 5 sensors per $km^2$.

Each sensor $3_i$, $1 \leq i \leq I$ measures an analyte concentration, for example an analyte concentration, at various times of day. The measurements are carried out at measurement times. The measurement times are distributed through the day and night, the measurements generally being carried out at regular time intervals, every hour or every two hours, for example.

The sensors $3_i$ are connected to a processing unit 4, which collects the measurements carried out at each measurement time, so as to establish a map of the analyte concentration in the geographical region in question, and optionally to generate a forecast map.

The geographical region 1 also contains at least one measurement station 5, referred to as the reference station. Unlike the sensors $3_i$, which are compact and inexpensive sensors, the reference station 5 is a fixed station that takes precise measurements during the day and at night. Generally, the geographical region contains a plurality of reference stations $5_k$, the index k being an integer comprised between 1 and $N_k$, $N_k$ corresponding to the number of reference stations in the geographical region in question. Each reference station $5_k$ is connected to a data collection network 6, the latter publishing the measured values. In FIG. 1, three reference stations $5_{k=1}$, $5_{k=2}$ and $5_{k=3}$, each symbolized by one triangle, have been shown. A reference station $5_k$ may, for example, be operated by a public operator, aiming to publish data relating to air pollution. In the European Union, the air pollution data center, operated by the European Environment Agency, publishes data, called open data, measured by fixed measurement stations. As mentioned in connection with the prior art, such reference stations provide quality measurements, but their cost and their bulk limit their number. Such a station takes the form of a unit, provided with devices for sampling ambient air, which are generally placed at the top of the unit. Inside the unit analyzers specific to certain analytes, such as those listed above, are found.

An important aspect of the disclosure is the use of open data, generated by reference stations $5_k$, to calibrate the sensors $3_i$.

Figure 2A:
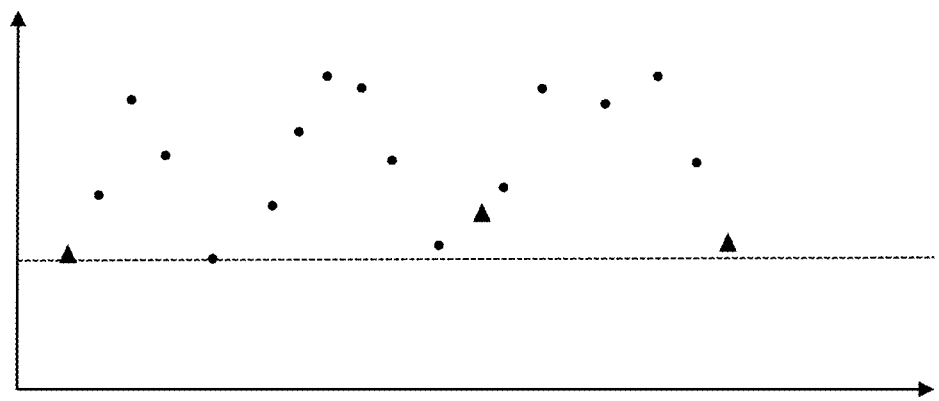
FIG. 2A illustrates the diurnal variability in the concentrations of a pollutant as a function of the geographical position of the gas sensors.
Figure 2B:
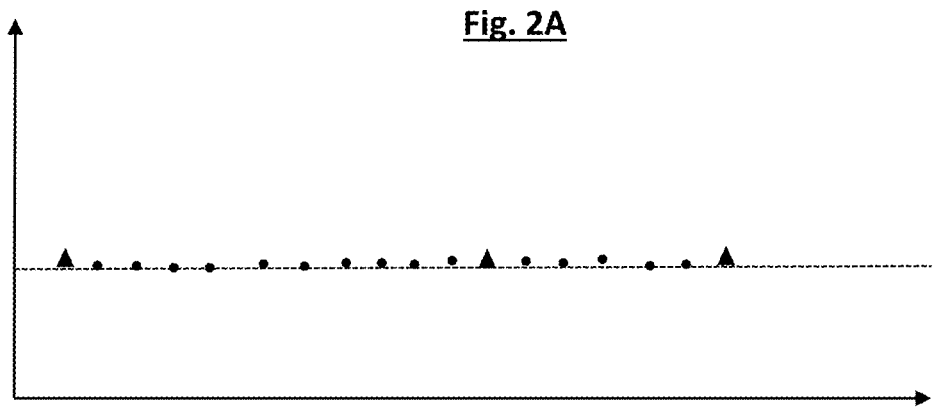
FIG. 2B illustrates the nocturnal variability in the concentrations of a pollutant as a function of the geographical position of the gas sensors.

FIGS. 2A and 2B illustrate concentrations of an analyte (in the present case $NO_2$) measured by gas sensors $3_i$ and reference stations $5_k$ at a measurement time during the day and at the end of the night, respectively. In these figures, the y-axis represents a measured analyte concentration, the x-axis representing a position of each sensor or reference station. Measurements taken by a gas sensor $3_i$ have been represented by a black dot. Measurements taken by a reference station $5_k$ have been represented by a black triangle. It may be seen that, during the day, the measurements taken by the gas sensors fluctuate. During the night, and more particularly at the end of the night, before the resumption of human activities, the measurements tend to coalesce to an ambient level. The ambient level has been represented by a dashed line in FIGS. 2A and 2B. The ambient level corresponds to a level of pollution that is considered uniform in the studied geographical region. It is due to the homogenization of local emissions and to pollutants diffusing from the vicinity of the geographical region in question, wind being one diffusion factor. The concentration homogenization at the end of the night has been shown for $NO_2$, but this observation is valid for any pollutant related to human activity, and, in particular, to road or air traffic, district heating or other cyclical industrial activities.

Fixed reference stations are conventionally divided into background stations, which are located relatively far from the main sources of pollution, and proximity stations, which are placed in proximity to sources of pollution. For example, the city of Grenoble has about ten reference stations: certain reference stations are considered to be background stations, and other reference stations are considered to be proximity stations. Yet other reference stations are considered to be intermediate stations, i.e., stations somewhere between a proximity station and a background station. FIGS. 3A to 3D show a variation, as a function of the time of day, in the average differences in $NO_2$ concentrations measured by two different reference stations, respectively. In other words, it is a question of average daily profiles representing average differences in concentrations measured, each hour, by two different reference stations. The hourly averages were calculated over a 7-month period, extending from January 2018 to July 2018. In each of these figures, the x-axis is the time of day (between 0 h and 24 h), and the y-axis is an $NO_2$ concentration.

Figure 3A:
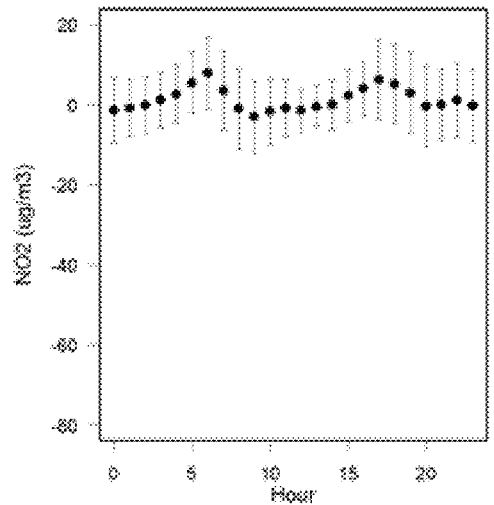
FIG. 3A shows an average daily profile, for a period of 7 months, of hourly concentration differences between two reference stations.
Figure 3B:
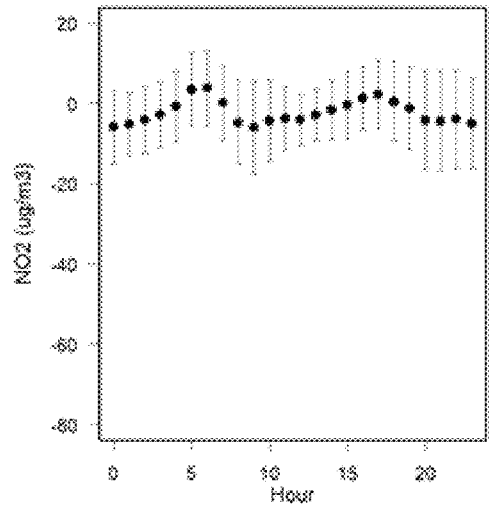
FIG. 3B shows an average daily profile, for a period of 7 months, of hourly concentration differences between two reference stations.
Figure 3C:
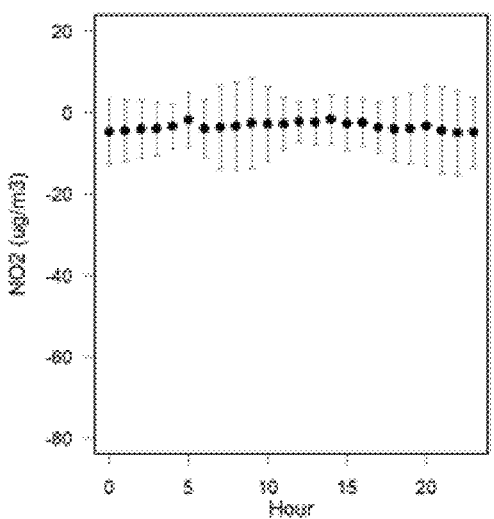
FIG. 3C shows an average daily profile, for a period of 7 months, of hourly concentration differences between two reference stations.
Figure 3D:
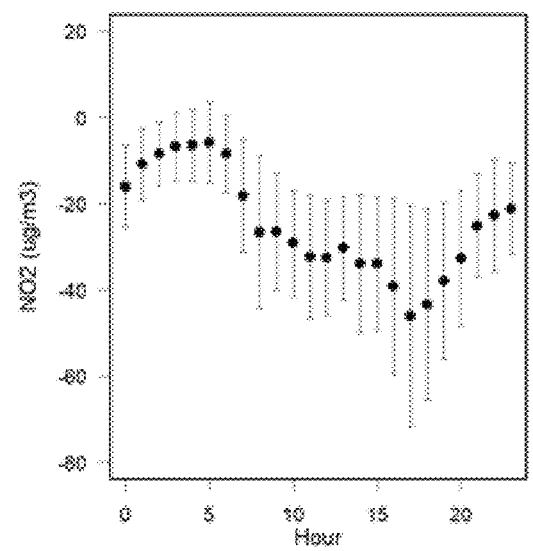
FIG. 3D shows an average daily profile, for a period of 7 months, of hourly concentration differences between two reference stations.

FIGS. 3A and 3B show daily profiles of average differences in the concentrations measured by an intermediate station and a first background station and a second background station, respectively. FIG. 3C represents the daily profile of the average differences in the concentrations measured by two background stations. FIG. 3D represents a daily profile of the average differences in the concentrations measured by the intermediate station and a proximity station.

It may be seen that, at the end of the night, that is to say between 2 o'clock and 6 o'clock in the morning, or between 2 o'clock and 5 o'clock in the morning, in each of the figures, the differences in the concentrations measured are small: their absolute value is lower than 10 µg/m³. It may therefore be concluded that during this time slot the analyte concentration may reasonably be considered to be uniform, the emission of the analyte being minimal. This confirms that the time slots between 2 o'clock and 6 o'clock, or between 2 o'clock and 5 o'clock, may be considered to be time slots conducive to the calibration of sensors 3, arranged in the vicinity of the reference stations $5_k$. Use is made of the fact that the reference stations $5_k$ publish, via the network 6, open data that are easily accessible to the public. The sensors may therefore be calibrated using the public data transmitted by the reference stations. The time slot employed for the calibration may correspond to a slot in which various reference stations measure a uniform analyte concentration.

Figure 4A:
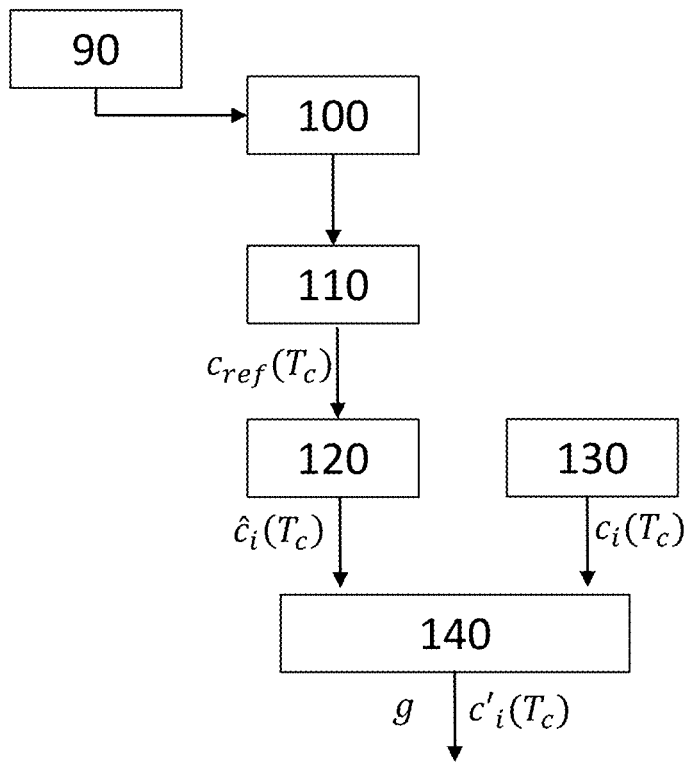
FIG. 4A shows the main steps of a calibrating method according to the disclosure.

FIG. 4A illustrates the main steps of a method for calibrating a gas sensor $3_i$, according to the disclosure.

Step 100: associating a gas sensor 3, with a reference station $5_k$. When the geographical region 1 in question contains a plurality of reference stations, the reference station $5_k$ most representative of the gas sensor may be selected. Such a selection, for example, takes into account the distance between each reference station and the gas sensor. The selection may also take into account other proximity parameters such as the direction and speed of the wind, or the topology of the geographical region in question, in order to determine the reference station that is closest in light of the proximity parameters in question. In FIG. 1, the wind has been represented by a vector V.

According to one variant, the gas sensor may be associated with a plurality of reference stations, as described below.

The selection of the reference station or of the reference stations associated with the gas sensor may be made in a calibrating step 90, which is described below.

Step 110: taking into account a reference analyte concentration $c_{ref}(T_c)$ measured by reference station $5_k$, in a calibration time slot. Use is made of the fact that the measurement is available via the public network to which the reference station is connected. The calibration time slot corresponds to a time slot in which the variability in the analyte concentration, in the geographical region in question, is minimal. Thus, it is considered that the analyte concentration, in the position of the gas sensor, may be estimated from the measurement taken by the reference station.

Step 120: estimating the analyte concentration at the geographical position occupied by the gas sensor, from the measurement delivered by the reference station. According to a first approach, the analyte concentration in the position occupied by the gas sensor is considered to be equal to the analyte concentration $c_{ref}(T_c)$ measured by the reference station. This assumption is valid when, in the calibration time slot, the distribution of the analyte is particularly uniform. According to a second approach, the analyte concentration in the position occupied by the gas sensor is obtained by applying a dispersion model on the basis of the measurement delivered by the reference station. An example of a dispersion model known to those skilled in the art is the Operational Street Pollution Model (usually designated by the acronym OPSM), which is a street canyon dispersion model.

Thus, if $c_{ref}(T_c)$ is an analyte concentration, obtained from the reference station, during the calibration time slot, and $\hat{c}_i(T_c)$ is an analyte concentration estimated at a position i of a gas sensor $3_i$:

$$\hat{c}_i(T_c) = c_{ref}(T_c) \quad (1)$$

or $$\hat{c}_i(T_c) = f(c_{ref}(T_c)) \quad (2)$$

f denoting a dispersion model.

Step 130:

Measuring the analyte concentration $c_i(T_c)$ with the gas sensor, during the calibration time slot. This measurement is performed at a measurement time belonging to the calibration time period. It is not necessarily the same as the reference time at which the reference concentration $c_{ref}(T_c)$ is measured. However, the measurement time and the reference time both belong to the calibration time slot.

According to one variant, the reference concentration $c_{ref}(T_c)$ is established by averaging the concentrations measured by the reference station during the calibration time slot. The analyte concentration $c_i(T_c)$ may also be determined by averaging concentrations measured by the gas sensor during the calibration time slot.

Step 140: Calibrating the Gas Sensor

In this step, the analyte concentration $c_i(T_c)$ measured by the sensor $3_i$ during the calibration time slot $T_c$ is compared with the concentration $\hat{c}_i(T_c)$ estimated in step 120, and the gas sensor $3_i$ is calibrated depending on the comparison.

If $c_i'(T_c)$ is the analyte concentration at the end of the calibration, $$c_i'(T_c) = g(c_i(T_c), \hat{c}_i(T_c)) \quad (3)$$

where g is the calibration function, the latter depending on $c_i(T_c)$ and on $\hat{c}_i(T_c)$. The calibration function g may be linear, such that $$c_i'(T_c) = a + bc_i(T_c), \quad (4)$$

a and b being real numbers.

Because of the calibration, the concentration $c_i'(T_c)$ established after the calibration is assumed to be more accurate than the concentration $c_i(T_c)$ measured prior to the calibration.

According to one simple example, b=1 and $$a = c_i(T_c) - \text{mean}(\hat{c}_i(T_c) - c_i(T_c)) \quad (5)$$

where mean $(\hat{c}_i(T_c) - c_i(T_c))$ is a mean of the difference $\hat{c}_i(T_c) - c_i(T_c)$ during a plurality of calibration time slots, for example the calibration slots of the last n days, n for example being comprised between 2 and 10. Considering a mean of the difference between the value $\hat{c}_i(T_c)$ estimated and the value $c_i(T_c)$ measured in a plurality of calibration slots allows the impact of noise generated by the sensor $3_i$ to be decreased.

The comparison of $\hat{c}_i(T_c)$ and $c_i(T_c)$ may take the form of a difference, as indicated above, but also of a ratio.

Steps 100 to 140 are performed periodically, for example every day, or every week.

According to one embodiment, the calibration is performed only in the presence of a wind the speed of which is higher than a preset threshold. Specifically, wind is considered to be an additional factor in the homogenization of the analyte concentration before or during the calibration time period/slot.

According to one variant of the embodiment described above, the gas sensor is calibrated using a plurality of reference measurement stations. It may, for example, be a question of the K reference stations $5k$ that are closest in light of proximity parameters such as distance and/or wind direction and speed and/or the topography of the geographical region in question. K is a natural number higher than 1. The estimate $\hat{c}_i(T_c)$ may be obtained by taking a weighted average of the reference measurements $c_{ref,k}(T_c)$ delivered by the K reference measurement stations in question. The index k, such that $1 \leq k \leq K$ corresponds to a reference station taken into account.

The method described above may comprise a training step 90, in which the reference station, or the reference stations, the measurements of the analyte concentration of which are the most correlated with the analyte concentration in the position of the measurement sensor, is or are selected. The training step may also allow the calibration time slot $T_c$ most conducive to carrying out the calibration to be estimated. It is a question of the time slot in which the estimate $\hat{c}_i(T_c)$ of the analyte concentration in the position of the sensor is considered to be the most reliable. The training step may also allow the estimate $\hat{c}_i(T_c)$ of the analyte concentration in the position of the gas sensor to be defined on the basis of the measurements $c_{ref,k}(T_c)$, respectively, generated by each selected reference station.

According to one embodiment, the training step is based on a machine-learning algorithm. It may notably be a question of a neural-network algorithm. This type of architecture, which is known to those skilled in the art, comprises an input layer IN, comprising the input data, at least one intermediate layer HID, or hidden layer, and an output layer OUT, which comprises the quantity to be estimated, in the present case the analyte concentration $\hat{c}_i(T_c)$ at the gas sensor. For example, only one intermediate layer will be considered.

The input data, which form the input layer IN, comprise the analyte concentrations $c_{ref,k}(T_c)$ respectively measured by each reference station $5k$ in question. The input layer IN may comprise other input data, for example measurements of other analytes, that are considered to be correlated with the analyte that it is being sought to quantify. The other measurements may also comprise atmospheric parameters, chosen, for example, from temperature, humidity, wind direction, and wind speed.

The intermediate layer HID forms at least one hidden layer, comprising nodes $y_j$ or neurons. The number of nodes may be set arbitrarily by a person skilled in the art, or during the training step. The number of hidden layers may also be set in the training step. Each node $y_j$ corresponds to a weighting factor $w_{k,j}$ determined in the training step, which is applied to each input datum $c_{ref,k}(T_c)$. The architecture of the neural network may be configured using a dedicated algorithm in the MATLAB environment or the PYTHON environment.

The training allows, inter alia, the weighting factors of the hidden layer to be set. In the example in question, the hidden layer comprises 30 nodes. Each node is related to an input datum by a weighting factor and a bias.

Figure 4B:
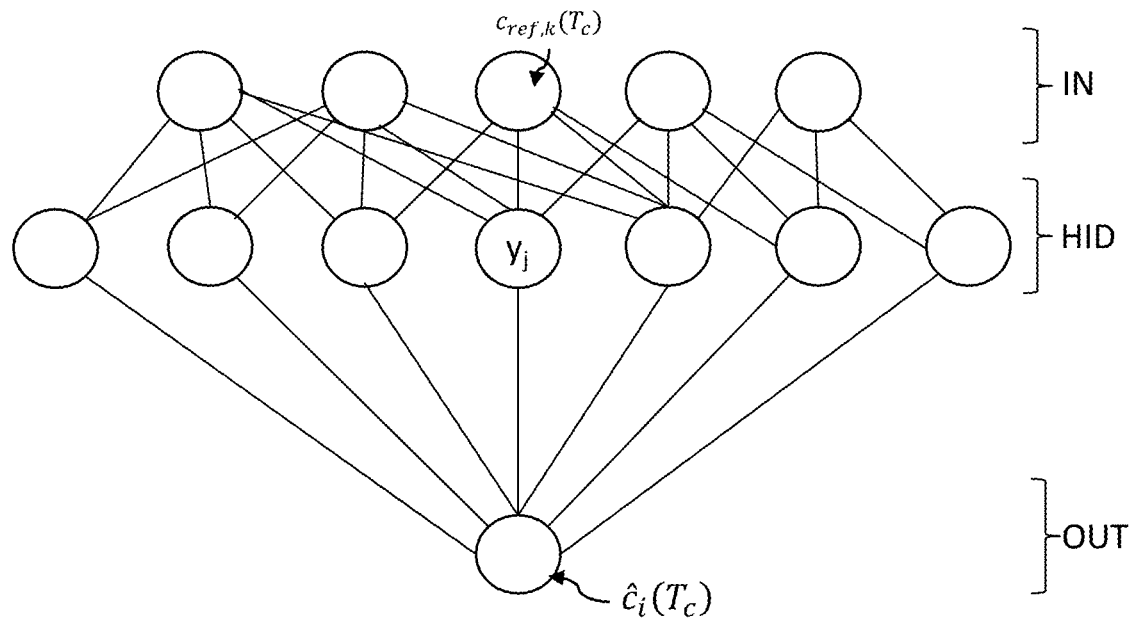
FIG. 4B shows an example of an architecture of a neural-network estimator.

FIG. 4B schematically shows one example of an architecture of a neural network comprising 3 layers:

the input layer IN, comprising the input data $c_{ref,k}(T_c)$;

the hidden HID layer, comprising the nodes (or neurons) $y_j$.
  The index j is an integer comprised between 1 and $N_j$, $N_j$ being an integer generally higher than or equal to 10, and which may exceed 1000; and the output layer OUT, comprising the estimate $\hat{c}_i(T_c)$.

Each node of the intermediate layer is linked to each input datum. In FIG. 4B, not all of the links have been shown, for the sake of clarity.

The algorithm is implemented by the processing unit 4. The algorithm uses measured physical data corresponding to the analyte concentrations $c_{ref,k}(T_c)$ mentioned above and the other input data mentioned above.

To each node $y_j$ is attributed a weighting factor $w_{k,j}$ associated with an input datum $x_k$. Thus, each weighting factor $w_{k,j}$ is associated with one input datum $c_{ref,k}(T_c)$ and with one node $y_j$. To each node is also attributed a bias value $w_{0,j}$. The weighting factors $w_{k,j}$ and the bias $w_{0,j}$ of each node are determined during the calibration. Each node $y_j$ implements an activation function f, such that:

$$y_j = f_j\left(w_{0,j} + \sum_k w_{k,j} c_{ref,k}(T_c)\right) \quad (6)$$

The form of each activation function $f_j$ is determined by a person skilled in the art. It may be, for example, a question of an activation function $f_j$ that is a hyperbolic-tangent function. The values of each node $y_j$ are combined to estimate the output variable $\hat{c}_i(T_c)$.

In the calibration step, the various parameters of the algorithm, in the present case the weighting factors, the biases, and the activation functions, are defined on the basis of test data. The test data are, on the one hand, the analyte-concentration values measured at each reference station, and, on the other hand, the analyte-concentration value measured at the gas sensor, preferably using a high-accuracy detector.

The calibration may also allow the reference stations with the best predictive power, i.e., the K reference stations the measurements of which are most significantly correlated with the analyte concentration in the position of the gas sensor, to be selected. Likewise, the calibration may also be used to determine the most appropriate calibration time slot $T_c$, i.e., the time slot in which the estimation of $\hat{c}_i(T_c)$ is the most accurate.

According to a more refined model, the output layer may comprise an estimate $\hat{c}_i(T_c)$ of an amount of analyte at various geographical positions, each position corresponding to a different gas sensor. The output layer then comprises as many data as there are gas sensors to be calibrated.

At the end of the training step, the steps 100 to 140 described above are implemented:

in step 100, the gas sensor $3_i$ is associated with the reference stations $5k$ selected during training;

in step 110, the reference concentrations $c_{ref,k}(T_c)$ measured by the K selected reference stations, and any other of the input data described above, are taken into account; and in step 120, the neural network is used to estimate the analyte concentration $\hat{c}_i(T_c)$ in the position of the gas sensor, steps 130 and 140 are similar to those previously described.

Trials

Trials have been carried out in the city of Grenoble, which contains the reference stations described above. During the trial phase, a gas sensor was placed in the same position as the intermediate reference station. In this example, the analyte in question was ozone ($O_3$). The gas sensor was calibrated every day by implementing the steps described above, the calibration time slot being comprised between 3 o'clock and 5 o'clock in the morning. The trials took place between Jun. 20, 2018 and Jul. 31, 2018. The calibration was carried out using equation (5).

Figure 5:
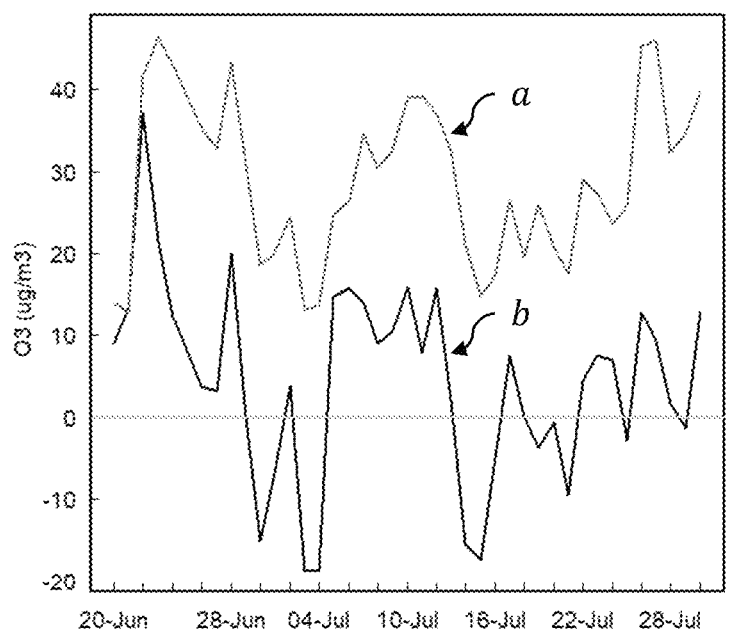
FIG. 5 shows the effect of a calibration of a gas sensor according to the disclosure.

FIG. 5 shows the variation over time in the difference between the daily averages provided by the reference station and the daily averages provided by the gas sensor:

without implementing the calibration (curve a), i.e., based only on an initial calibration carried out before installation of the gas sensor; and implementing the calibration every day (curve b).

In the first few days, curves a and b are almost coincident. However, after a few days, curves a and b clearly diverge from each other, due to the regular calibration of the gas sensor. The measurements obtained by the reference station are considered to be accurate.

A mean of the values represented by each curve was calculated, the mean being 29.13 µg/m$^3$ for curve a and 4.56 µg/m$^3$ for curve b. This shows that by carrying out regular calibrations of the sensor, the concentrations measured by the latter become more representative of reality.

Embodiments of the disclosure make it possible to perform a clever calibration of a gas sensor, using published data delivered by reference stations distributed over the territory in question. The calibration is performed remotely, based on measurements resulting from the gas sensor and on an estimate of an analyte concentration in the position occupied by the gas sensor. The calibration does not require any physical intervention on the gas sensor, and does not require the latter to be exposed to a standard gas. Since the calibration is particularly simple, it may be carried out frequently, for example every day or every week.

Embodiments of the disclosure will possibly be used to calibrate gas sensors distributed over an urban or peri-urban environment, or along a main road, or about an airport, or even in the vicinity of an industrial plant.

The invention claimed is:

1. A method for calibrating a gas sensor, the gas sensor belonging to a network of sensors distributed between various positions in a geographical region, the gas sensor being intended to measure a concentration of an analyte in the air at various measurement times, the geographical region comprising at least one reference station, which is remote from the gas sensor, the reference station being intended to measure, at various reference times, a concentration of analyte in the air, the method comprising:

a) associating at least one reference station with the gas sensor;
  b) during a calibration time slot, measuring an analyte concentration with the gas sensor and measuring an analyte concentration with each reference station associated with the gas sensor;
  c) from the measurement of the analyte concentration measured by each reference station associated with the gas sensor, in the calibration time slot, estimating an analyte concentration in the position of the gas sensor;

d) comparing the analyte concentration estimated in c) and the analyte concentration measured by the gas sensor in b);

e) calibrating the gas sensor using on the comparison made in d);

wherein:

the analyte is emitted, in the geographical region, at a concentration that varies over the course of a day, the emitted analyte concentration varying between a minimum and a maximum over the course of each day;

the calibration time slot is determined so as to correspond to a minimum emission of the analyte in the geographical region in question, during each day.

2. The method of claim 1, wherein, in c), the analyte concentration in the position of the gas sensor is:

considered to be equal to the analyte concentration measured by a reference station associated with the gas sensor;

or estimated by applying a dispersion model, based on the analyte concentration measured by the at least one reference station associated with the gas sensor.

3. The method of claim 1, wherein:

the geographical area comprises a plurality of reference stations;

step a) comprises associating a reference station to the gas sensor depending on a distance between the gas sensor and each reference station.

4. The method of claim 1, wherein a) comprises associating a reference station to the gas sensor depending on the speed of a wind propagating through the geographical region, and/or depending on the direction of the wind propagating through the geographical region.

5. The method of claim 1, wherein the analyte is: NO or $NO_2$ or $O_3$ or $SO_2$ or CO or $C_6H_6$ or particulate matter.

6. The method of claim 1, wherein, in e), the sensor is calibrated by implementing a calibration function, applied to the comparison carried out in step d).

7. The method of claim 1, wherein each reference station is connected to a public database, such that, in b), the analyte concentration measured by the reference station is taken from the public database.

8. The method as claimed in claim 1, comprising, prior to steps a) to e), a training step so as to:

select a reference station or a plurality of reference stations, from among a plurality of reference stations, such that, during the calibration time slot, the analyte concentration measured by each selected reference station is correlated with the analyte concentration in the position of the gas sensor;

determine an estimator of the analyte concentration in the position of the gas sensor from the analyte concentration measured by each selected reference station;

such that:

in a), each reference station selected in the training step is associated with the gas sensor;

in c), the analyte concentration in the position of the gas sensor is estimated by applying the estimator determined in the training step.

9. The method of claim 8, wherein the calibration time slot is determined in the training step.

10. The method of claim 8, wherein the training step employs a neural network, so as to select at least one reference station and establish the estimator.

11. The method of claim 1, wherein:

the analyte is emitted by vehicles or heating plants;

the calibration time slot is comprised between midnight and 6 o'clock in the morning.

12. The method of claim 11, wherein the calibration time slot is comprised between 3 o'clock in the morning and 6 o'clock in the morning.

13. A device for estimating a concentration of an analyte in a geographical region, the device comprising:

a plurality of gas sensors distributed over the geographical region, each gas sensor being configured to measure an analyte concentration at various measurement times, a processing unit, which receives the measurements of at least one gas sensor;

wherein the processing unit is configured to calibrate the gas sensor by implementing the method of claim 1, using at least one reference measurement station located in the geographical region.

* * * * *

UNITED STATES PATENT AND TRADEMARK OFFICE
CERTIFICATE OF CORRECTION

PATENT NO. : 11,879,881 B2
APPLICATION NO. : 17/416057
DATED : January 23, 2024
INVENTOR(S) : Benjamin Lebegue Page 1 of 1

It is certified that error appears in the above-identified patent and that said Letters Patent is hereby corrected as shown below:

In the Specification

Column 6, Line 11, change "sensors 3, arranged" to --sensors 3$_i$ arranged--
Column 6, Line 22, change "sensor 3, with a" to --sensor 3$_i$ with--

Signed and Sealed this
Twenty-fourth Day of December, 2024

Derrick Brent
*Acting Director of the United States Patent and Trademark Office*